United States Patent
Determan et al.

(10) Patent No.: US 8,098,900 B2
(45) Date of Patent: Jan. 17, 2012

(54) SKIN DETECTION SENSOR

(75) Inventors: Gary E. Determan, Maple Grove, MN (US); David J. Wunderlin, New Hope, MN (US)

(73) Assignee: Honeywell International Inc., Morristown, NJ (US)

( * ) Notice: Subject to any disclaimer, the term of this patent is extended or adjusted under 35 U.S.C. 154(b) by 971 days.

(21) Appl. No.: 11/715,244

(22) Filed: Mar. 6, 2007

(65) Prior Publication Data

US 2008/0219514 A1 Sep. 11, 2008

(51) Int. Cl.
*G06K 9/00* (2006.01)

(52) U.S. Cl. ........ 382/115; 382/116; 382/117; 382/124; 382/191; 340/5.52; 340/5.53; 340/5.82; 340/5.83

(58) Field of Classification Search .................. 382/115, 382/116, 117, 124, 191; 340/5.52, 5.53, 340/5.82, 5.83; 902/3, 4
See application file for complete search history.

(56) References Cited

U.S. PATENT DOCUMENTS

| | | | |
|---|---|---|---|
| 5,088,817 A * | 2/1992 | Igaki et al. | 356/71 |
| 5,103,486 A * | 4/1992 | Grippi | 382/116 |
| 5,366,454 A * | 11/1994 | Currie et al. | 604/890.1 |
| 5,906,582 A * | 5/1999 | Kondo et al. | 600/500 |
| 6,274,086 B1 * | 8/2001 | Wilson et al. | 422/82.08 |
| 6,324,419 B1 * | 11/2001 | Guzelsu et al. | 600/476 |
| 6,556,269 B1 * | 4/2003 | Takiar et al. | 349/150 |
| 6,675,095 B1 * | 1/2004 | Bird et al. | 701/301 |
| 6,886,964 B2 * | 5/2005 | Gardiner et al. | 362/276 |
| 6,992,718 B1 * | 1/2006 | Takahara | 348/333.09 |
| 7,167,734 B2 * | 1/2007 | Khalil et al. | 600/310 |
| 7,263,213 B2 * | 8/2007 | Rowe | 382/124 |
| 7,347,365 B2 * | 3/2008 | Rowe | 235/382 |
| 7,440,597 B2 * | 10/2008 | Rowe | 382/124 |
| 7,442,682 B2 * | 10/2008 | Kitaura et al. | 514/3 |
| 7,460,696 B2 * | 12/2008 | Rowe | 382/124 |
| 7,508,965 B2 * | 3/2009 | Rowe et al. | 382/127 |
| 7,545,963 B2 * | 6/2009 | Rowe | 382/124 |
| 7,627,151 B2 * | 12/2009 | Rowe | 382/124 |
| 7,668,350 B2 * | 2/2010 | Rowe | 382/124 |
| 7,751,594 B2 * | 7/2010 | Rowe et al. | 382/115 |
| 2002/0009213 A1 * | 1/2002 | Rowe et al. | 382/115 |
| 2002/0183624 A1 * | 12/2002 | Rowe et al. | 600/476 |
| 2003/0023151 A1 * | 1/2003 | Khalil et al. | 600/309 |
| 2003/0035301 A1 * | 2/2003 | Gardiner et al. | 362/583 |
| 2003/0142856 A1 * | 7/2003 | McClurg et al. | 382/124 |
| 2004/0073119 A1 * | 4/2004 | Mycek et al. | 600/476 |

(Continued)

OTHER PUBLICATIONS www.wikipedia.com—Definition of Light Emitting Diode.*

(Continued)

*Primary Examiner* — Jason M Repko
*Assistant Examiner* — Mia M Thomas
(74) *Attorney, Agent, or Firm* — Luis M. Ortiz; Kermit D. Lopez; Melissa Asfahani

(57) ABSTRACT

A device for detecting the presence of human skin including an illuminator source for providing an IR band at a predetermined frequency known as a blue LED. The IR band frequency ranges from about 400 nanometers (nm) to about 500 nm, and preferably from about 450 nm to about 485 nm. Most preferred is a blue LED with a frequency of about 468 nm. The band is reflected off a target and received by a sensor such as a photo detector. The value for human skin is compared to the signal detected. Other materials that have been used to spoof detectors have different values and thus are distinguished from human skin.

15 Claims, 1 Drawing Sheet

U.S. PATENT DOCUMENTS

| | | | |
|---|---|---|---|
| 2004/0125996 A1* | 7/2004 | Eddowes et al. | 382/128 |
| 2004/0158300 A1* | 8/2004 | Gardiner | 607/88 |
| 2005/0053264 A1* | 3/2005 | Amano et al. | 382/115 |
| 2005/0135102 A1* | 6/2005 | Gardiner et al. | 362/276 |
| 2005/0238208 A1* | 10/2005 | Sim | 382/115 |
| 2005/0271258 A1* | 12/2005 | Rowe | 382/124 |
| 2006/0092315 A1* | 5/2006 | Payonk et al. | 348/370 |
| 2006/0115128 A1* | 6/2006 | Mainguet | 382/115 |
| 2006/0229520 A1* | 10/2006 | Yamashita et al. | 600/503 |
| 2006/0274921 A1* | 12/2006 | Rowe | 382/124 |
| 2006/0276712 A1* | 12/2006 | Stothers et al. | 600/438 |
| 2006/0281992 A1* | 12/2006 | Stothers et al. | 600/438 |
| 2007/0012931 A1* | 1/2007 | Lee et al. | 257/89 |
| 2007/0030475 A1* | 2/2007 | Rowe et al. | 356/71 |
| 2007/0191719 A1* | 8/2007 | Yamashita et al. | 600/503 |
| 2007/0200663 A1* | 8/2007 | White et al. | 340/5.31 |
| 2008/0107309 A1* | 5/2008 | Cerni | 382/115 |
| 2008/0203307 A1* | 8/2008 | Determan et al. | 250/341.8 |
| 2008/0297788 A1* | 12/2008 | Rowe et al. | 356/300 |
| 2008/0304712 A1* | 12/2008 | Rowe et al. | 382/115 |
| 2010/0008545 A1* | 1/2010 | Ueki et al. | 382/115 |
| 2010/0069897 A1* | 3/2010 | Spikker et al. | 606/9 |
| 2010/0174229 A1* | 7/2010 | Hsu et al. | 604/66 |

OTHER PUBLICATIONS www.wikipedia.com—Definition of Photodiode/Phototransistor.*
Chen et al. "Biometric System of High Sensitivity Absorption" IEEE ICSS Feb. 2005 International Conference on Systems and Signals, pp. 1-6.*
Charlot et al. "A Sweeping Mode Integrated Fingerprint Sensor with 256 Tactile Microbeams" Journal of Microelectromechanical Systems, vo. 13, No. 4, Aug. 2004, pp. 1-9.*
Barral et al. "Fake Fingers in Fingerprint Recognition: Glycerin Supersedes Gelatin" LNCS 5458 pp. 57-69 (2009).*
Antonelli et al. "Fake Finger Detection by Skin Distortion Analysis" IEEE Transactions on Info Forensics and Security vo.1, No. 3 Sep. 2006 pp. 1-14.*
K.A. Nixon, R.K. Rowe, J. Allen, S. Corcoran, L. Fang, D. Gabel, D. Gonzales, R. Harbour, S. Love, R. McCaskill, B. Ostrom, D. Sidlauskas, K. Unruh; Novel Spectroscopy-Based Technology for Biometric and Liveness Verification; Proceedings of SPIE vol. 5404, Apr. 12, 2004; pp. 287-295.
R. Jenkins; Spectral Face Profiling; Biometric Technology Today, SJB Services, Somerton, GB; vol. 13, No. 6, Jun. 1, 2005 PCT—Notification of Transmittal of the International Search Report and the Written Opinion of the International Searching Authority, or the Declaration, Date of Mailing: Jun. 30, 2008.

* cited by examiner

SKIN DETECTION SENSOR

FIELD OF THE INVENTION

The present invention relates to skin detection sensors. More particularly, the invention relates to such sensors where a specific source is employed to detect the presence of human skin while distinguishing over other materials that may be used as substitutes for human skin and, thus, defeat or spoof the sensor.

BACKGROUND OF THE INVENTION

This invention may be related to U.S. patent application Ser. No. 11/264,654, filed Oct. 31, 2005, entitled "Skin Detection Sensor," the disclosure of which is incorporated herein in its entirety. In that application, two IR bands are directed at a target proposed to be human skin. One IR band is capable of being reflected from skin and the other is absorbed by skin. When both conditions exist, skin is detected as being present.

The invention may be related to U.S. patent application Ser. No. 10/987,806, filed Nov. 12, 2004, and entitled "Infrared and Visible Fusion Face Recognition System". The invention may also be related to U.S. patent application Ser. No. 10/946,748, filed Nov. 12, 2004, and entitled "Infrared Face Detection and Recognition System". These above-mentioned patent applications are incorporated herein by reference. The assignee of these patent applications is the same assignee of the present invention.

Other related patent documents may include U.S. Pat. No. 6,370,260 B1, issued Apr. 9, 2002, entitled "Near-IR Human Detector", and by Pavlidis et al.; U.S. Pat. No. 6,718,049 B2, issued Apr. 6, 2004, entitled "Near-Infrared Disguise Detection", and by Pavlidis et al.; and U.S. patent application Ser. No. 10/077,672, filed Feb. 15, 2002, entitled "Near-Infrared Method and System for Use in Face Detection", and by Pavlidis et al.; all of which are incorporated herein by reference. The assignee of these patent documents is the same assignee of the present invention.

Current biometric sensors based on measuring fingerprint identity or hand geometry sensors are of significant interest to a variety of industries and applications. The security industry is constantly seeking sensors that identify certain specific persons to allow access to a secured area, a device such as a computer or other electronic equipment, or a cell phone. This industry is growing and thus is still encountering new issues.

However, biometric sensors that rely on a particular property of a person, such as a fingerprint, can be defeated. If a rubber cast or cutout of a fingerprint is used, the device will recognize the correct print, even if it is not being used by the person to whom it belongs. Photographs of irises have been used to thwart iris detection. Thus, access to secure property would be compromised.

However, biometric sensors that rely on a particular property of a person, such as a fingerprint, can be defeated. If a rubber cast or cutout of a fingerprint is used, the device will recognize the correct print, even if it is not being used by the person to whom it belongs. Photographs of irises have been used to thwart iris detection. Thus, access to secure property would be compromised. Recently it has been suggested that fingerprint sensors used for biometrics can be and have been spoofed by a variety of fake finger materials. An actual valid fingerprint is obtained, perhaps illegally, and is transferred to another material that has similar properties to human skin. When a sensor is used to validate the fingerprint, first determining if the fingerprint is on human skin, present day sensors cannot distinguish between real skin and some other materials.

One successful effort to defeat a fingerprint reader has been reported, where a finger print was taken from a glass using a digital photo of it, printing it on a transparency, and then using the print as an overlay to etch the fingerprint on to a surface. A finger was then molded using a gelatin material such as that found in Gummy Bears candy. This replicated finger tricked or defeated a fingerprint reader 80% of the times it was tested. Tests against eleven different commercially available fingerprint biometric systems resulted in a finding that all of the systems could be deceived by the Gummy Bear replicated finger.

It would be a great advance in the art if a device could be provided that would accurately identify the presence of human skin in a situation where an individual's specific and unique characteristic, such as a fingerprint, could then be recognized.

It would be another advantage in the art if the presence of human skin could be determined in a manner that prevents other materials from responding to these signals in the same manner.

Yet another advantage would be if a device could be provided that would be easy to use to permit or deny access to the biometric sensor.

Other advantages will appear hereinafter.

SUMMARY OF THE INVENTION

It has now been discovered that the above and other advantages of the present invention may be obtained in the following manner. Specifically, the present invention provides a device for detecting the presence or absence of human skin.

The device includes an illuminator source for providing a light source having a frequency associated with blue LED light. The frequency of the blue LED light ranges from about 400 nanometers (nm) to about 500 nm and preferably between about 450 nm to about 485 nm. Most preferred is blue LED light having a frequency of about 468 nm. The illuminator source is positioned to direct said blue LED light source on to human skin or other objects presented as skin.

A detector is positioned to receive the blue LED light after it has contacted the skin to provide a signal indicating the voltage of the reflected light source. A detector processing unit compares the signal with a known value indicating the presence of human skin. Preferred detectors are photodiodes and phototransistors.

If the signal values are the same, within the tolerance desired, that is indicated and used in further processing. For example, the positive detection of human skin can be used to turn on other devices such as fingerprint detectors that determine the particular fingerprint against data stored and compared for authorized and unauthorized persons.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
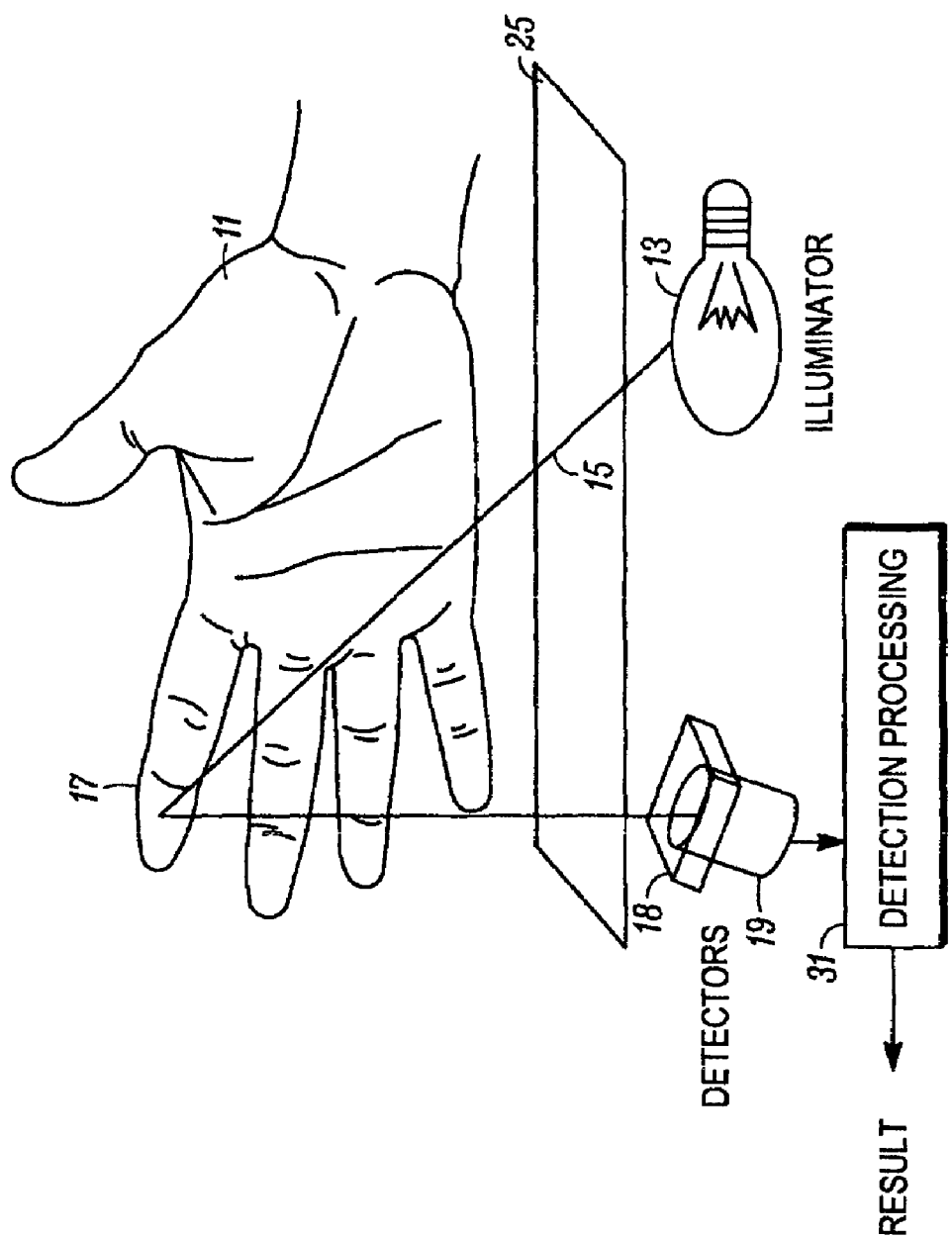
FIG. 1 is a schematic view of the preferred embodiment of the present invention.

The present invention operates as a sensor to detect the presence of skin, such as that of the human finger or other part of the anatomy that is exposed to detection. In the preferred embodiment, a hand 11, as shown in FIG. 1, is Illuminated by Illuminator 13, which transmits light on a path 15 that strikes the skin of finger 17 and is reflected back to a photo detectors 19.

The light 15 transmitted from illuminator 13 is in the band range of a blue LED with a frequency associated with blue LED light that reflects from human skin. The frequency of the blue LED light ranges from about 400 nanometers (nm) to about 500 nm and preferably between about 450 nm to about 485 nm. Most preferred is blue LED light having a frequency of about 468 nm.

Detector 19 is positioned to receive the blue LED light 15 after it has contacted the skin of finger 17 to provide a signal indicating the voltage of the reflected light source. A detector processing unit compares the signal with a known value indicating the presence of human skin. Preferred detectors are photodiodes and phototransistors.

A detection processing element 31, which may be a chip or other microelectronic device, performs a comparison of the output from detector 19 with known values. It may also be desirable to place a filter 18 in the path of light beam 15 as it enters the detector 19 to eliminate interfering light.

The present invention is admirably suited to improve many of the current biometric sensors currently in use or envisioned for use as a security device, access control or other use. Fingerprint sensors are able to compare a presented fingerprint against a data base, to allow or deny access to a controlled area or use of an electronic device such as a computer, cell phone, or other device, for example. But fingerprint sensors are not capable of distinguishing between a human finger presented for fingerprint screening and a rubber or plastic mold of the same finger. The present invention would verify the presence or absence of human skin, and thus make the fingerprint sensor much more reliable. Iris comparisons also can be defeated by the use of contact lenses in some cases. Again, the present invention would verify the presence of actual skin. In one use of the present invention, the biometric sensor would need to have a positive determination of the presence of human skin from the device of this invention before even processing the data it has been designed to detect.

In order to demonstrate the efficacy of the present invention, a number of experiments were performed. Specifically, a variety of light sources were tested to determine the reflective properties of a variety of materials including human skin. A human finger was used since this invention is admirably suited for use with fingerprint detectors.

Presented below in Table I are the results of tests of seven different light sources, including visible and IR frequencies. The sensors that were tested were at frequencies ranging from 468 nm to 1500 nm. There were two different sensors used for detecting the reflected light. One is a InGaAs Photodiode with a frequency range of 900 nm to 1700 nm. The other is a Hermetic Silicon Phototransistor with a frequency range of approximately 400 nm to 1100 nm. The materials tested are also listed in Table I.

TABLE I

| | \multicolumn{7}{c}{Sample Voltages} |
|---|---|---|---|---|---|---|---|
| | green 520-550 nm | blue 468 nm | red 641-700 nm | yellow 585-600 nm | IR 950 nm | 1300 nm sensor 55-753 | 1500 nm sensor 55-753 |
| No Sample | 0.0058 | 0.056 | 0.056 | 0.0059 | 0.107 | 0.99 | 0.26 |
| Finger | 0.0250 | 2.600 | 0.370 | 0.0260 | 0.630 | 3.11 | 0.34 |
| Nylon | 0.0120 | 1.220 | 0.100 | 0.0169 | 0.240 | 1.35 | 0.35 |
| Clear Gummy | 0.0197 | 0.870 | 0.130 | 0.0250 | 0.320 | 2.50 | 0.32 |

TABLE I-continued

| | \multicolumn{7}{c}{Sample Voltages} |
|---|---|---|---|---|---|---|---|
| | green 520-550 nm | blue 468 nm | red 641-700 nm | yellow 585-600 nm | IR 950 nm | 1300 nm sensor 55-753 | 1500 nm sensor 55-753 |
| Red Gummy | 0.0120 | 1.220 | 0.200 | 0.0090 | 0.320 | 2.70 | 0.39 |
| Green Gummy | 0.0250 | 0.410 | 0.160 | 0.0140 | 0.320 | 2.60 | 0.35 |
| Yellow Gummy | 0.0280 | 0.690 | 0.160 | 0.0250 | 0.400 | 2.70 | 0.39 |
| Delrin | 0.0500 | 4.490 | 0.320 | 0.0500 | 0.940 | 3.30 | 0.5 |
| White Teflon | 0.0600 | 4.600 | 0.630 | 0.0890 | 1.217 | 3.45 | 0.59 |
| Blue silicon | 0.0280 | 4.550 | 0.230 | 0.0290 | 1.300 | 3.65 | 0.96 |
| Nitrile | 0.0163 | 4.560 | 0.210 | 0.0220 | 1.680 | 3.60 | 0.84 |
| Latex | 0.0720 | 4.500 | 0.630 | 0.0830 | 1.730 | 3.68 | 0.86 |
| PVC Tube | 0.0820 | 4.560 | 0.660 | 0.0830 | 1.840 | 3.72 | 1.12 |
| Wood Dowel | 0.0670 | 4.400 | 0.720 | 0.0800 | 1.890 | 3.68 | 0.87 |
| Leather Gloves | | 0.780 | 0.065 | | 1.47 | | 0.39 |

In Table I, the results are obtained by measuring the output voltage of each detector from the source as it reflects off the different materials. Presented below in Table II is a mathematical conversion of the data in Table I. Specifically, in Table II, the results from Table I are normalized by subtracting out the No Sample data and then by dividing by the total range of the data.

TABLE II

| | \multicolumn{7}{c}{Percent of Change} |
|---|---|---|---|---|---|---|---|
| | green 520-550 nm | blue 468 nm | red 641-700 nm | yellow 585-600 nm | IR 950 nm | 1300 nm | 1500 nm |
| No Sample | 0% | 0% | 0% | 0% | 0% | 0% | 0% |
| Finger | 25% | 56% | 47% | 24% | 29% | 78% | 9% |
| Nylon | 8% | 26% | 7% | 13% | 7% | 13% | 10% |
| Clear Gummy | 18% | 18% | 11% | 23% | 12% | 55% | 7% |
| Red Gummy | 8% | 26% | 22% | 4% | 12% | 63% | 15% |
| Green Gummy | 25% | 8% | 16% | 10% | 12% | 59% | 10% |
| Yellow Gummy | 29% | 14% | 16% | 23% | 16% | 63% | 15% |
| Delrin | 58% | 98% | 40% | 53% | 47% | 85% | 28% |
| White Teflon | 71% | 100% | 86% | 100% | 62% | 90% | 38% |
| Blue silicon | 29% | 99% | 26% | 28% | 67% | 97% | 81% |
| Nitrile | 14% | 99% | 23% | 19% | 88% | 96% | 67% |
| Latex | 87% | 98% | 86% | 93% | 91% | 99% | 70% |
| PVC Tube | 100% | 99% | 91% | 93% | 97% | 100% | 100% |
| Wood Dowel | 80% | 96% | 100% | 89% | 100% | 99% | 71% |
| Leather Gloves | | 16% | 1% | | | 18% | 15% |

While some materials in Table II, such as PVC tube, can be distinguished from a human skin such as a finger, other materials are not distinguished with some of the light sources. For example, as seen above, the yellow LED at about 585 to 600 nm has a value for the finger of 24% and the clear Gummy and yellow Gummy have a value of 23% each. This supports the prior work where Gummy materials defeated fingerprint detectors. At 1500 nm, the finger data was 9% and clear and green Gummy were 7% and 10% respectively.

Because the results of the blue LED tests are different from the other frequencies, data can be presented in graph form to demonstrate the distinctive results from the blue LED against all the materials tested.

The value for the finger comes in at about 56% and it is isolated from the rest of the materials. Thus the detector processor unit receiving data from the device of this invention will identify real skin data from a finger and is capable of distinguishing it from all of the other materials including the Gummy material previously found to defeat skin detectors. All other data are far from the value for real skin.

While particular embodiments of the present invention have been illustrated and described, it is not intended to limit the invention, except as defined by the following claims.

The invention claimed is:

1. A biometric device for detecting a presence of human skin rather than a gelatin-based candy used to mimic human skin, comprising:
an illuminator source for providing a blue LED light source at a frequency of approximately 468 nanometers, wherein said blue LED light source is reflected from human skin;
a photodiode detector for receiving said blue LED light source after said blue LED light source has contacted said human skin and for providing a signal representative of said blue LED light source after said blue LED light source is reflected from said human skin;
a detector processing unit for comparing said signal with a known reflectivity value of human skin and a known reflectivity value of said gelatin-based candy used to mimic human skin, indicating said presence of said human skin if said signal matches said known reflectivity value of human skin, and positively determining said presence of said human skin prior to processing data collected from said biometric device; and
a data processing unit that processes data collected from said human skin, wherein said data processing unit allows access to a controlled area or electronic equipment if said human skin indicates that an associated human is allowed access to said controlled area or said electronic equipment.

2. The biometric device of claim 1, wherein said photodiode detector is a part of a phototransistor detector.

3. The biometric device of claim 1, wherein data processing comprises comparing fingerprints detected from said human skin to a database of collected fingerprint information.

4. The biometric device of claim 1, wherein data processing comprises comparing an iris detected using said detection unit to a database of collected iris information.

5. The biometric device of claim 1 wherein said electronic equipment comprises at least one of the following types of electronic equipment: a computer or a mobile communications device.

6. A biometric device for detecting a presence of human skin rather than a gelatin-based candy used to mimic human skin, comprising:
illuminator source means for providing a blue LED light source at a frequency of approximately 468 nanometers, wherein said blue LED light source is reflected from human skin;
photodiode detector means for receiving said blue LED light source after said blue LED light source has contacted said human skin and for providing a signal representative of said blue LED light source after said blue LED light source is reflected from said human skin;
detector processing unit means for comparing said signal with a known reflectivity value of human skin and a known reflectivity value of said gelatin-based candy used to mimic human skin, indicating said presence of said human skin if said signal matches said known reflectivity value of human skin, and positively determining said presence of said human skin prior to processing data collected from said biometric device; and
data processing unit means for processing data collected from said human skin, wherein said data processing unit allows access to a controlled area or electronic equipment if said human skin indicates that an associated human is allowed access to said controlled area or said electronic equipment.

7. The biometric device of claim 6, wherein said photodiode detector means is a part of a phototransistor detector means.

8. The biometric device of claim 6, wherein data processing comprises comparing fingerprints detected from said human skin to a database of collected fingerprint information.

9. The biometric device of claim 6, wherein data processing comprises comparing an iris detected using said detection unit to a database of collected iris information.

10. The biometric device of claim 6 wherein said electronic equipment comprises at least one of the following types of electronic equipment: a computer or a mobile communications device.

11. A method for detecting a presence of human skin rather than a gelatin-based candy used to mimic human skin, comprising the steps of:
providing a blue LED light at a frequency of approximately 468 nanometers, wherein said blue LED light source is reflected from human skin;
directing said blue LED light source against an object proposed to be said human skin;
positioning a photodiode detector to receive said blue LED light source after said blue LED light source has contacted said human skin and to provide a signal representative of said blue LED light source after said blue LED light source is reflected from said human skin;
comparing said signal with a known reflectivity value of human skin and a known reflectivity value of said gelatin-based candy used to mimic human skin, indicating said presence of said human skin if said signal matches said known reflectivity value of human skin, and positively determining said presence of said human skin prior to processing data collected from said biometric device, whereby a value outside of said known value indicates a presence of a material other than said human skin; and
processing data collected from said human skin, wherein data processing unit allows access to a controlled area or electronic equipment if said human skin indicates that an associated human is allowed access to said controlled area or said electronic equipment.

12. The method of claim 11, wherein said photodiode detector is a part of a phototransistor detector.

13. The method of claim 11, wherein data processing comprises comparing fingerprints detected from said human skin to a database of collected fingerprint information.

14. The method of claim 11, wherein data processing comprises comparing an iris detected using said detection unit to a database of collected iris information.

15. The method of claim 11 wherein said electronic equipment comprises at least one of the following types of electronic equipment: a computer or a mobile communications device.

* * * * *